United States Patent [19]
Del Bon et al.

[11] Patent Number: 5,355,873
[45] Date of Patent: Oct. 18, 1994

[54] AN INHALATION DEVICE AND METHOD HAVING A VARIABLY RESTRICTABLE AIR INLET THAT ALLOWS THE INHALATION FORCE REQUIRED TO OVERCOME A LOCKING ELEMENT TO BE CHANGED

[76] Inventors: Franco Del Bon, Eggenacherstrasse 52, CH-4663 Aarburg; Walter Treyer, Dorngasse 43, CH-8967 Widen, both of Switzerland

[21] Appl. No.: 871,979

[22] Filed: Apr. 22, 1992

[51] Int. Cl.$^5$ .................. A61M 11/00; A61M 15/08; A63B 23/00; A62B 7/00
[52] U.S. Cl. .................. 128/200.23; 128/200.24; 128/203.24; 128/203.25; 482/13
[58] Field of Search ............ 128/200.14, 200.18, 128/200.21, 200.22, 200.23, 200.24, 203.12, 203.15, 203.23, 203.24, 207.14, 207.16, 203.25; 482/13; 222/14, 17, 20, 59, 634, 635, 372, 321, 385; 239/338, 339, 360, 370

[56] References Cited

U.S. PATENT DOCUMENTS

| | | | |
|---|---|---|---|
| 2,549,303 | 4/1951 | Friden | 128/203.15 |
| 2,579,280 | 12/1951 | Trumbour et al. | 128/203.15 |
| 3,565,070 | 2/1971 | Hanson et al. | 128/173 |
| 3,598,294 | 8/1971 | Hedrick et al. | 222/402.2 |
| 3,732,864 | 5/1973 | Thompson et al. | 128/200.23 |
| 3,789,843 | 2/1974 | Armstrong et al. | 128/200.23 |
| 4,114,608 | 9/1978 | Russo | 482/13 |
| 4,444,202 | 4/1984 | Rubin et al. | 482/13 |

FOREIGN PATENT DOCUMENTS

| | | | |
|---|---|---|---|
| 238363 | 11/1958 | Australia | 128/200.23 |
| 52958 | 10/1970 | Australia | 128/200.23 |
| 0147028 | 7/1985 | European Pat. Off. | |
| 0411714 | 2/1991 | European Pat. Off. | 482/13 |
| 40542 | 7/1932 | France | |

*Primary Examiner*—Kimberly L. Asher
*Attorney, Agent, or Firm*—Longacre & White

[57] ABSTRACT

The method described relates to conditional dosing and nebulisation of a liquid or powdered preparation for inhalation. The condition for dosing and nebulisation of the preparation is that the inhaling person must produce an inhalation power according to his or her constitution and which is sufficient for an optimum effect of the inhaled preparation. Without this minimum inhalation power, no dosing and no nebulisation of the preparation is possible. The corresponding inhalation device comprises a known device for dosing and nebulising (without condition) and additional means which inhibit actuation of the device by positive locking until the minimum inhalation power is produced by the inhaling person. A preferred embodiment has, for dosing and nebulisation, a reservoir with a dosing and nebulising pump and, for said positive locking, a ball (13), which is loosely housed in a corresponding ball chamber (14). Upon inhalation, an air stream is generated through the ball chamber (14), which moves the ball (13) out of its locking position, into which it is driven by the force of gravity. so that the positive locking mechanism is released and the pump can be actuated manually.

16 Claims, 7 Drawing Sheets

AN INHALATION DEVICE AND METHOD HAVING A VARIABLY RESTRICTABLE AIR INLET THAT ALLOWS THE INHALATION FORCE REQUIRED TO OVERCOME A LOCKING ELEMENT TO BE CHANGED

The invention belongs to the field of medicine technology and relates to a method and device for dosing and nebulizing a preparation for inhalation by means of which, for example, pharmaceutical products such as antiasthmatic drugs can be inhaled in a dosed manner.

Inhalation is a known method of administering medicines, for example, for absorption into the airways and lungs. Various inhalation devices are commercially available for this purpose, with which liquid or powdered preparations are introduced, finely distributed, into the buccal cavity. The inhalation devices are so conceived that with each application a specified dose of the preparation is released. In order that the preparation, finely distributed by nebulization, can pass from the buccal cavity, through the throat into the airways and lungs, it is inevitable that the patient must inhale simultaneously whilst introducing the nebulized preparation into the buccal cavity by means of the inhalation device. If he or she does not do so, or does so insufficiently, the medicine remains wholly or partly in the buccal cavity and in the throat, and the desired effect is not achieved. Even if the medicine can be precisely dosed with the inhalation device, the dose of medicine which is actually effective is dependent on the strength of the actual inhalation, i.e. on the strength of simultaneous inhalation. The part of the dose remaining on the walls of the buccal cavity and throat is substantially swallowed and remains virtually ineffective. In the case of only weak inhalation, the effective dose is only a fraction of the dose released by the inhalation device. Every inhaler user is familiar with this failure of the effect of inhalation and is inclined to achieve the desired effect with a further dose.

Inhalation devices have also been developed which only permit a dose and nebulization if inhalation takes place at the same time. Such devices are described, for example, in U.S. Pat. Nos. 3,565,070, 3,789,843 and 3,598,294 or in French Patent 40542. All these devices must be brought into an active state before inhalation by a separate lever. In this active state, an automatic dose is released by inhalation. All these devices include, in addition to a supply vessel for the inhalation preparation, a complex mechanism consisting of a lever and spring system and are therefore elaborate and, in particular, prone to malfunctioning.

Such disadvantages do not affect the inhalation device described in European Pat. 0 147 028, in which dosing is actuated manually, but a corresponding locking device ensures that this is only possible when the patient inhales. This device also comprises a mechanism, albeit less complex, which consists of a plurality of levers, but which is located partly in the region of the spray to be inhaled and is therefore exposed to contamination which may jeopardise its perfect functioning.

All existing devices comprise, for dosing and nebulizing, a reservoir, which contains the preparation and a propellant gas and which is provided with a dosing valve, with which a specified dose of the preparation is nebulized per stroke. Different dosages for different patients, for example adults and children, are achieved by inhalation of a different number of individual doses. If the device, as mentioned above, has to be actuated again in between individual doses, operation seems complicated. As they are intended to be applicable for patients with different constitutions, the devices are also adapted for the weakest patients, i.e. children for example, who according to their smaller lung capacity can only produce a slight inhalation power, which is however sufficient for a good effect in their own case. In other words, if for example an adult uses the same device, although he or she must inhale to release or unlock the dose, this does not have to be carried out with sufficient strength for optimum inhalation according to his or her lung capacity. Therefore, whilst all existing devices remove from the patient the synchronization of dosing and inhalation, only in the minority of cases do they force the patient to produce adequate inhalation power for an optimum effect of the preparation.

The object of the invention, therefore, is to indicate a method of dosing and nebulizing inhalation preparations whereby each dose released is also an effective dose. the patient being forced to inhale upon dosing and with a strength corresponding to his or her constitution. In the method according to the invention, the patient is not only to be forced to inhale sufficiently. but should also be given the opportunity to train his or her lung power by inhaling in order to help improve his or her inhalation. In emergencies, however, it should also be possible to administer the dose with insufficient inhalation. The preparation is to be dosed and nebulized according to known methods and be so prepared by appropriate pretreatment after being discharged from the nebulizing nozzle that, if possible, it only contains particles or drops of an optimum size for inhalation and is present in the inhaled air, if possible, in the form of a stable aerosol.

The configuration of the inhalation device for carrying out the method is to be adaptable for different users and adjustable for training the lung power. It should be as small as possible and simple to operate. It should comprise simple, reliably operating mechanical parts which are not prone to contamination. It should allow the patient absolute control over the administration of a dose. The device should be usable for the nebulization and dosing of standard commercial inhalation preparations or active substances in standard commercial aerosol containers with a dosing valve, but especially in devices with mechanical dosing and nebulising pumps which operate without propellant gas.

The method and device are described in detail with the aid of the following Figures, which show:

FIG. 1 (*a* and *b*), a comparison of the released and active doses in the use of a non-inhalation-dependent method and of the inhalation-dependent method according to the invention, and a diagram for the training effect of the method according to the invention, FIG. 2 (*a* and *b*), sections through an embodiment, given by way of example, of the inhalation device according to the invention to illustrate its operation, FIG. 3, a plan view towards the nozzle of the embodiment, according to FIG. 2, FIG. 4 (*a* to *d*), respective details from the section and plan view in FIGS. 2 and 3 for two embodiments with an adjustable inhalation strength, FIG. 5 (*a* to *c*), three embodiments, by way of example, of the mouthpiece of the device according to the invention, FIG. 6 (*a* and *b*), a further embodiment of the device according to the invention, FIG. 7 (a and b), parts to be manufactured for two manufacturing processes for the device according to the invention.

The invention is based on the fact that adequate inhalation by the patient is made a condition of the dosing and nebulization of the preparation. If the patient does not inhale sufficiently strongly that the dose of nebulized preparation released by the force generated by inhaling can pass into the airways of the patient, then the dosing and nebulising device remains locked. Thus a wasted release of preparation just into the buccal cavity and on to the walls of the throat is avoided, and intentional or unintentional evasion of having to produce the necessary inhalation power is therefore impossible. The inhalation strength necessary to release the device is adjustable, so that the device can be configured to suit patients with different lung capacities and hence different potential lung power.

Due to this requirement and a corresponding further measure, the method of inhalation-dependent dosing and nebulization according to the invention also permits training to improve the lung power. If the doctor, for example, increases the necessary inhalation strength for a dose in a controlled manner when the patient is capable of achieving that strength, the inhaling person trains his or her lungs by the forced inhalation and thus increases the lung power and active lung capacity.

The method according to the invention uses (in terms of apparatus) a jet of the finest particles or droplets produced according to a known method, e.g. pumping through a nozzle or expansion of a propellant gas. The particles or droplets produced by this method have different sizes, of which only those with dimensions or between 1 and 5 $\mu m$ are suitable for inhalation. Furthermore, the particles or droplets, particularly when produced by pumps, have a relative speed compared to the surrounding air and therefore do not represent a proper aerosol. In a further embodiment, by suitable treatment of the particle or droplet jet directly after its discharge from the nozzle, the method according to the invention can effect separation of over-large particles and swirling of the jet in the surrounding air so that a stable aerosol is formed. By means of such treatment of the nebulized preparation before inhalation, the proportion of preparation that only passes into the airways and remains useless is further reduced.

The device for carrying out the method according to the invention comprises a partial device which is known per se, with which the preparation to be inhaled is dosed and nebulized, i.e. a reservoir with a manual dosing and nebulizing pump or a pressurised container with a dosing valve. In addition, there are parts according to the invention which lock the device by positive locking, until the positive locking mechanism is released by the air stream generated by the patient's inhalation and the device can be actuated, and parts according to the invention which are for pretreatment of the particle or droplet jet.

FIG. 1*a* shows how the inhalation-dependent method according to the invention differs from a non-inhalation-dependent process. The inhalation strength S is shown on the abscissa, and the size of dose D on the ordinate.

Let the dose aD released by the dosing and nebulising device have a constant size, which is dependent on the configuration of the device, which will not be discussed in more detail here, as the dosing and nebulization of a preparation for inhalation (without dependence on the latter) corresponds to the prior art.

Let the inhalation strength S be a measure of the suction power produced by the inhaling person and on which depends the amount of the released dose that reaches its destination in the airways or bronchi and has the desired effect, and the amount that remains in the buccal cavity and throat and therefore remains virtually ineffective. The curve wD. 1 shows how the effective dose rises with the strength of inhalation, until it reaches the dose released at an inhalation strength S.1. In other words, if the inhaling person applies a suction power S.1, provided that all the remaining peripheral conditions are optimally met, the whole dose released passes through the buccal cavity into the respiratory system and can be effective. The curve wD.1 together with the straight line aD (the broken and solid part) therefore represents a non-inhalation-dependent doing and inhalation method. The inhaling person administers a dose independent of the inhalation strength, but the effective dose is directly dependent on the inhalation strength. If the inhalation power is insufficient (wDu), an insufficient dose Du results. The part of the released dose between the curve wD. 1 and the straight line aD is ineffective and wasted.

The curve wD.2, together with the solid part of the straight line aD represents the inhalation-dependent method according to the invention for dosing and inhalation. Up to the region of an inhalation strength S.1, at which the whole dose released can be effective, no dosing is possible. At inhalation strengths of more than S.1, the dose can be varied as desired. With this method for dependent dosing and nebulisation according to the invention, no part of the dose released remains ineffective or is wasted; obviously assuming, even in this case, that nebulisation is optimal, i.e. the particles or droplets have a suitable size for inhalation and are present as an optimally stable aerosol.

The strength with which a person must inhale in order to inhale optimally depends on his or her constitution and especially on the lung capacity available to and actively used by him or her, i.e. the inhalation strength S.1 is to be placed at different points along the abscissa S according to each patient. In order that a suitable inhalation device is optimally applicable for various patients, it must be suitable configured or adjusted.

The active lung capacity for a child is approx. 2 to 3 l, and for a healthy adult approx. 4 to 6 l, and may rise to approx. 9 for an athlete, e.g. a racing cyclist, but for an asthmatic it may fall to approx. 2 to 3 l. In every case, the active lung capacity can be increased with appropriate breath training, which is especially desirable in the case of the asthmatic. The adjustability of the inhalation strength releasing the dose permits such training. The doctor or the patient himself or herself can then adjust this inhalation strength in such a way that it always corresponds to the maximum power of which he or she is capable and which he or she can train permanently and thereby increase by inhaling.

The combination of a manually released dose and inhalation-dependent locking of this dose offers the further advantage that the inhaling person is always aware of whether he or she has inhaled an effective dose or not. Since the release of the dose is triggered by manual action of the inhaling person, it is known to the inhaling person, and since every dose released is an effective one, the dose itself is also known in one way. In the case of an automatic dose released by inhalation.

as is described in some of the patents mentioned in the introduction, such simple checking is not possible. Even in the case of a non-inhalation dependent method (i.e. no power threshold), although the release of a dose is conscious (manual action), the size of the effective dose can only be estimated by means of irritation reactions in the throat, which are undesirable per se. Since such irritation reactions in the case of aerosols with very small particles or droplets, which are advantageous per se, is correspondingly weak, they are an unreliable indicator, and to avoid incorrect dosage (the release of a plurality of doses in the case of weak indication), it may be necessary to add an extra irritant. e.g. menthol, to the preparation to be inhaled, as an indicator of an effective dose. Since according to the inhalation-dependent method according to the invention each dose released is an effective one, even the finest aerosols can be used safely, either without additional indicators and without incorrect dosages, or indicators are used in any case to give the patient a sense of security (habit).

Figure 1A:
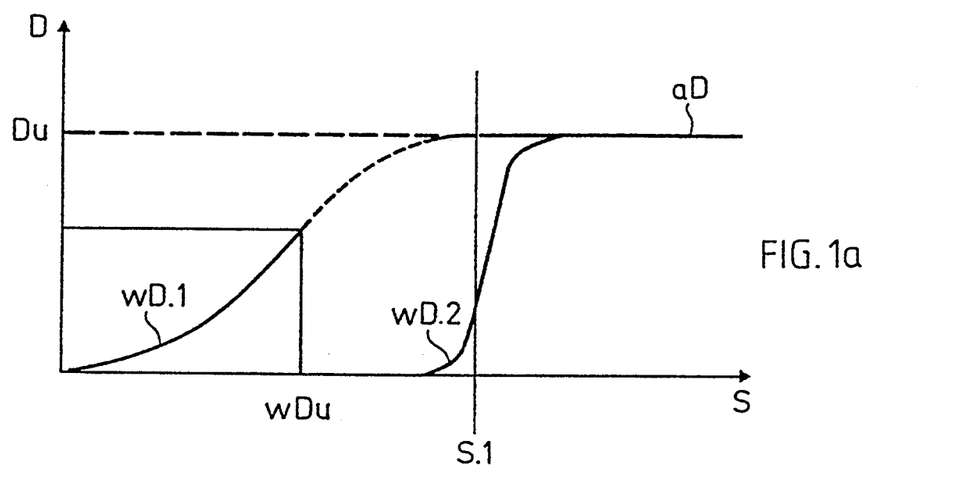
Figure 1B:
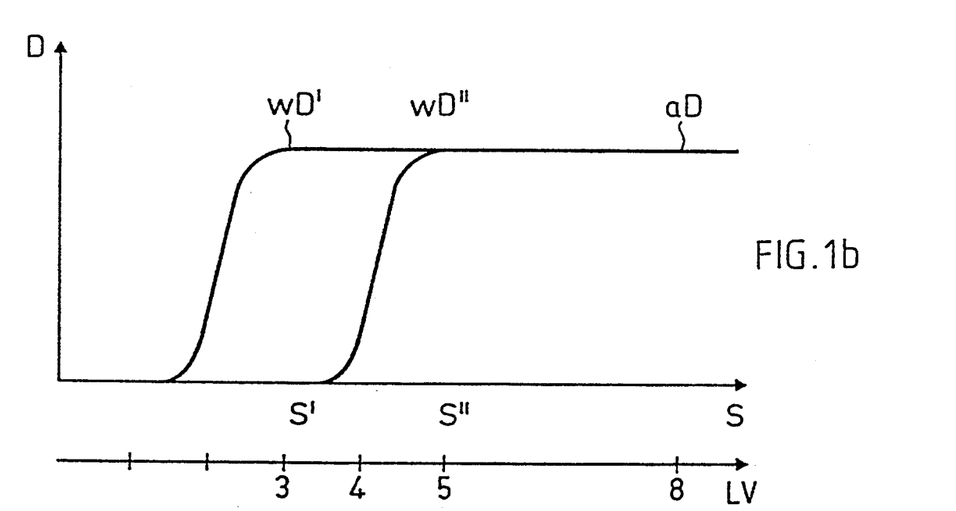

FIG. 1*b* shows schematically the effect of variability of the inhalation strength necessary for a dose. The curve wD′, which permits the release of a fully effective dose at an inhalation strength S′, is a good setting for an asthmatic who has an active lung capacity LV of only 3 l. If the patient increases his or her active lung capacity by inhaling, he or she may raise the inhalation requirements (see arrow) progressively by increasing the necessary inhalation strength S, until a setting wD″ is reached, for example, which corresponds to a lung capacity of 5 l.

FIG. 2*a* shows an embodiment of the device according to the invention, with which a dose of the inhalation preparation can be nebulized manually during simultaneous inhalation with a specified strength. At first, those components will be described which are purely for dosing and nebulizing, whose operation can be assumed in fact to be known, and which in the embodiment shown by way of example are formed as reservoirs with a nebulizing pump, i.e. an embodiment which has the advantage of operating without propellant gas.

The liquid preparation to be inhaled is contained in a reservoir 1, which has a rigid outer wall 1.1 and a deformable inner wall 1.2, between which an air cushion 1.3 is located, and which encloses a supply chamber 1.4. A suction tube 2 and a cylinder 3 integrally formed with the suction tube 2 are so mounted in the supply chamber 1.4 that the free end of the suction tube 2 lies close to the part of the wall of the reservoir 1 which is located at the bottom in the direction of gravity in the normal inhalation position. A further hollow piston 4 is coaxially mounted in the cylinder 3 in such a manner that it can slide on corresponding projections 3.1 of the cylinder in the direction of the common axis and that, together with these projections 3.1, it forms an inner, also coaxial spring chamber 5 which is connected by an axial bore 3.2 in the base of the cylinder 3 to the suction tube 2 and in which a spiral spring 6 is mounted. The spring chamber 5 is sealed tightly against the dosing chamber 7 when the pressure is equalized. Between the inner wall of the cylinder 3 and the outer wall of the inner piston 4, a substantially hollow cylindrical outer cavity is left, which forms the dosing chamber 7. This dosing chamber 7 is sealed tightly against the open end of the cylinder 3 by an outer piston 8, which is mounted coaxially with the inner piston 4 and the cylinder 3 and movably in the direction of the common axis. The outer piston 8 has an axial bore 8.1, which connects the dosing chamber 7 to the nozzle bore system 9.1 in a nozzle head 9 resting on the outer piston 8. The inner piston 4 carries on its side associated with the bore 8.1 an annular sealing face 4.1, and the outer piston 8 a corresponding sealing edge 8.2. The sealing face 4.1 and the sealing edge 8.2 are pressed on to one another by the force of the spring 6 in the state of equalized pressure. The pressure button 10 with which the dosing device is actuated is located on the nozzle head 9.

If the pressure button 10 is pressed against the reservoir 1, the outer piston 8 and the inner piston 4 are pressed via the nozzle head 9 into the cylinder 3 against the suction tube 2. Thus a relatively high pressure is produced in the dosing chamber 7, and a less high pressure in the spring chamber 5 and in the reservoir 1. Thus the inner piston 4 is pressed against the force of the spring, so that some of the preparation is forced into the bore 8.1 between the sealing face 4.1 and the sealing edge 8.2, and the pressure button 10 can be pressed further against the reservoir 1. Thus more preparation is conveyed out of the dosing chamber 7 towards the nozzle and the air cushion 1.3 is bore compressed. If the pressure button 10 is completely depressed, the pressure in the dosing chamber 7 falls and the sealing face 4.1 is again pressed on to the sealing edge 8.2. If the pressure button is then released, the spring 6 presses the inner and outer pistons (4 and 8), and therewith the nozzle head 9 and the pressure button 10, into their starting position. Thus a low pressure is created in the dosing chamber 7, due to which the preparation is sucked out of the spring chamber 5 between the inner piston 4 and the projection 3.1. Pressure equalization in the reservoir is effected by a ventilation valve (not shown) opening between the two walls 1.1 and 1.2. The device is thus back in the same position as before dosing, the supply chamber 1.4 has decreased by a small dose, and the space between the walls 1.1 and 1.2 has increased by one dose.

The nozzle head 9 carries a laterally mounted nozzle 9.2, through which the ejected dose is nebulized, and is housed in a housing 11, which is rigidly connected to the reservoir 1 and carries the mouthpiece 12 on the nozzle side. The pressure button 10 projects through a suitable aperture out of the housing 11. If the pressure button 10 is actuated, the nozzle head 9 moves relative to the housing 11 and the mouthpiece 12. Such relative motion can be prevented by a ball 13, which is housed loosely in a ball chamber 14, which extends over the separating face between the housing 11 and the nozzle head 9. If the ball 13 is in the position shown in FIG. 2*a*, i.e. in such a position that said separating face extends through the ball, it effects positive locking between the housing 11 and the nozzle head 9. The ball chamber 14 is inclined towards the force of gravity if the inhalation device is held in the inhalation position (reservoir 1 below, pressure button 10 above), so that the ball 13 is driven by the force of gravity into the positively locking position. The ball chamber 14 is so formed that air can circulate around the ball and the ball 13 can move freely therein as far as a stop 12.1, which separates the ball chamber 14 proper from its aperture into the interior of the mouthpiece 12 and prevents the ball 13 from being able to leave the ball chamber 14. The ball chamber 14 is open to the interior of the mouthpiece 12 on the one hand and to the outside on the other hand through an air channel 15 between the nozzle head 9 and the housing 11 and through an air hole 11.1 in the housing 11. The ball 13 is in its positively locking position on the opening of the air channel 15 into the ball chamber 14.

Figure 2A:
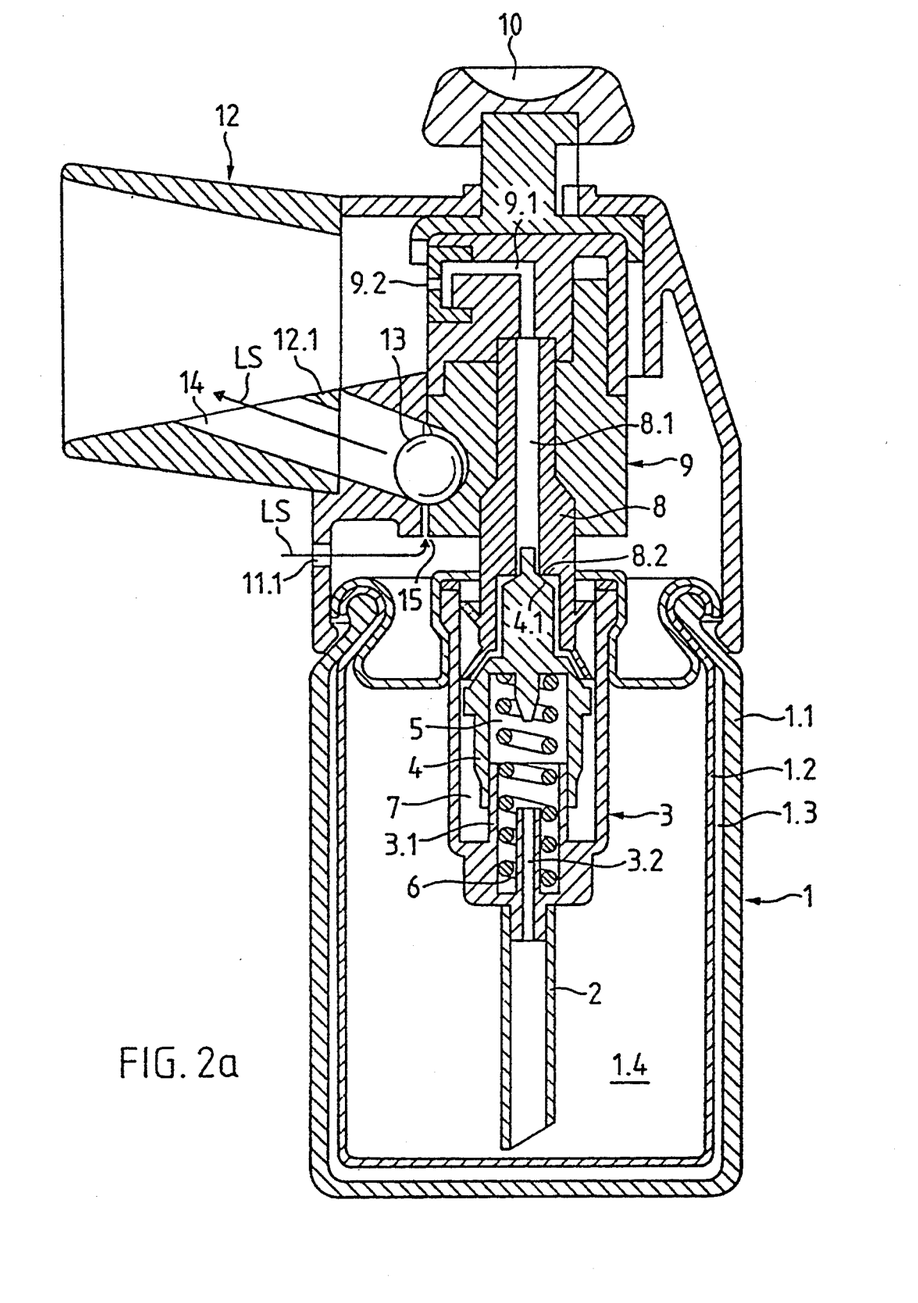

Only if the ball 13 is moved against the stop 12.1 in the ball chamber 14, and in particular sufficiently far that it no longer lies in the part of the ball chamber 14 recessed in the nozzle head 9, is relative motion between the housing 11 and the nozzle head 9, i.e. dosing and nebulization of the preparation, possible.

To inhale, the device is brought into the inhaling position reservoir 1 below, pressure button 10 above) the opening of the mouthpiece 12 is placed between the lips, and pressure is exerted on the pressure button 10 with one finger. If the inhaling person then breathes in, low pressure is created in the interior of the mouthpiece 12. The ball 13 is thereby lifted from the opening of the air channel 15 and air (arrows LS) flows through the air hole 11.1 and the air channel 15 into the ball chamber 14 and into the interior of the mouthpiece 12. If this air stream is strong enough, it moves the ball 13 against the stop 12.1 and thus the positively locking connection is undone. The force exerted on the pressure button 10 can then push the locking device against the housing, so that a dose of preparation is nebulized.

In an emergency, in which the patient needs a dose of the inhalant without being able to inhale sufficiently, the device can simply be used "upside-down", i.e. with the reservoir 1 above and the pressure button 10 below. In this position, the ball 13 cannot lock the device, as it is driven against the stop 12.1 by the force of gravity.

Figure 2B:
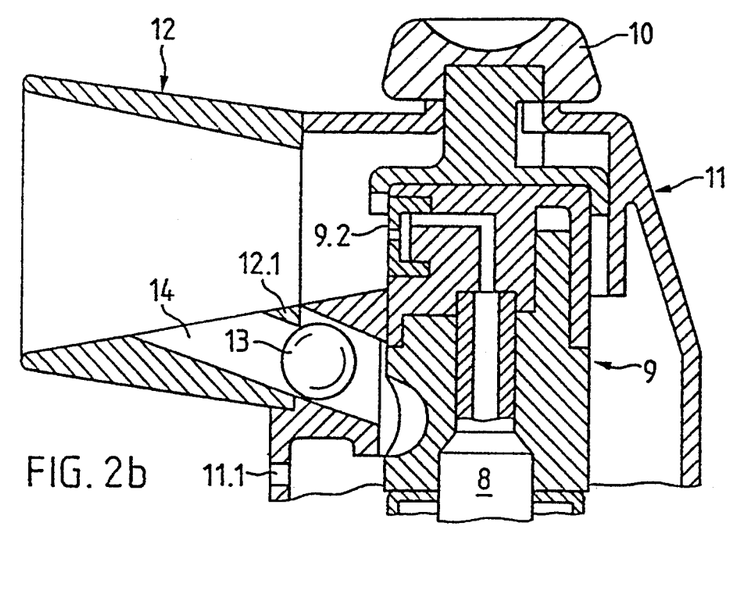

FIG. 2b shows the same inhalation device as FIG. 2a, but the pressure button 10 is in its depressed position. The ball 13 rests against the stop 12.1, the two parts of the ball chamber 14 are displaced towards one another, as the nozzle head 9 has been displaced relative to the housing 11. As soon as the air stream LS and the pressure on the pressure button 10 slackens, the nozzle head 9 moves back into its starting position in the housing 11 and the ball 13 falls back into the positively locking position driven by the force of gravity.

Figure 3:
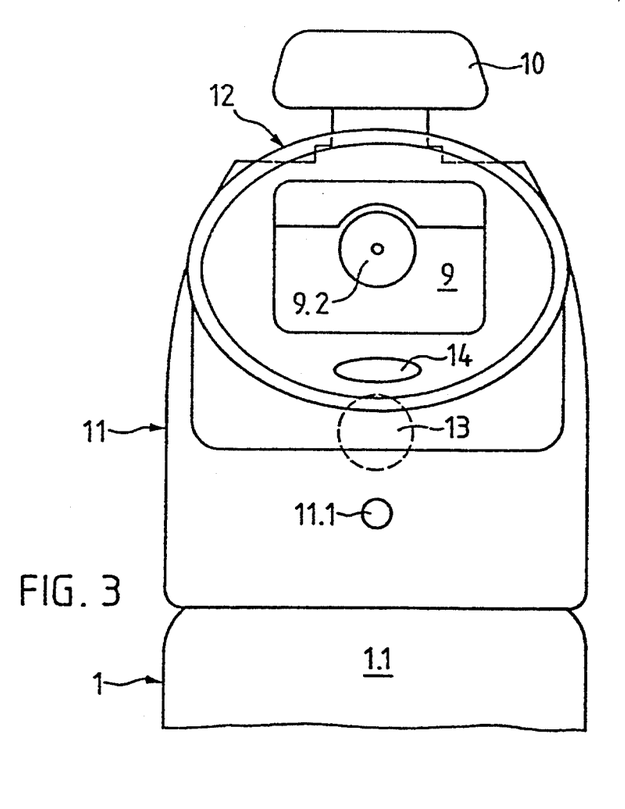

FIG. 3 shows a detail of a view of the inhalation device according to Figures 2a and 2b as a plan view towards the aperture of the mouthpiece 12. In this Figure, the mouthpiece 12 can be seen and, through its aperture, the nozzle head 9 with the nozzle 9.2. Below the nozzle 9.2, the opening of the ball chamber 14 into the interior of the mouthpiece 12 can be Seen and the ball 13, which is actually not visible, is indicated in its positively locking position. Below the ball 13 is the air hole 11.1.

The inhalation device shown in FIGS. 2 and 3 comprises, as positive locking means between the nozzle head and the housing, a ball, Which is moved in a corresponding aperture. This ball represents a simple positive locking means. It is mounted outside the region of the nebulized preparation and is therefore not exposed to any contamination which might impair its operation. Operation is conceivably simple. The device only needs to be brought into the inhalation position (reservoir 1 below, pressure button 10 above) and the ball is in its positively locking position. After inhalation, the ball automatically returns to this position. Therefore, no special lever is needed to actuate the device, which is a particular advantage in cases where a plurality of doses are to be inhaled. Adaptation of the device for various users is possible, for example, by inserting different sizes or weights of balls.

Obviously, the means for positive locking can take another form. According to the object of the device according to the invention, the positive locking means must meet the following requirements:

Positive locking must be effected by parts which are moved relative to one another during actuation of the dosing and nebulizing mechanism.

The positive locking means must be simple and so mounted that they are not contaminated by the nebulized preparation.

The positive locking device must be capable of being released by the force exerted by inhalation, in which case it must be possible to adjust the device to the minimum necessary force for such release.

Positive locking must be automatically reestablished as soon as this force ceases to act.

Other conceivable positive locking means are, for example, suitably formed springs or plates.

The embodiment of the inhalation device according to the invention described by way of example in connection with FIGS. 2 and 3 comprises, for dosing and nebulizing the preparation, a pump actuated by a pressure button. Other known devices can also be used, such as pumps of a different construction, for example, or pressurized containers with a dosing valve arid filled with propellant gas.

The embodiment of the inhalation device according to the invention described by way of example in connection with FIGS. 2 and 3 has no means for adjusting the inhalation strength necessary for a dose. This minimum inhalation strength necessary to release the dose and dependent on the configuration of the device is particularly determined by the size and weight of the ball 13 and by the smallest cross-sectional aperture between the air hole 11.1 and the opening of the ball chamber 14 into the interior of the mouthpiece 12, which acts as a choke. The heavier and smaller the ball and the smaller this minimum cross-sectional aperture, the higher the inhalation strength needed to release the positive locking device. To adapt thee device for different users, different sizes or weights of ball can be used, for example. Further, means for choking the air stream LS can be provided, for example, whose basic setting determines the configuration of the device and which can be further fine-tuned by the doctor or by the user for training purposes. Two embodiments of such choke devices given by way of example are shown in FIGS. 4a to 4d. In both cases, an adjustable choke in the form of a slide is mounted at the air hole FIGS. 4a and b show as a detail, in section like FIG. 2a, and in plan view like FIG. 3, the ball chamber 14 with the ball 13 in the positively locking position, the air channel 15 and the air hole 11.1. The air hole 11.1 is triangular in shape and carries a rotary slide 40, which can be rotated between the positions 40.1 and 40.2 and which is shown in FIG. 4b in the position (40.1) in which the inhalation strength necessary to release the positive locking device is the minimum. By rotation of the rotary slide 40 in the direction of the arrow, the necessary inhalation strength increases. The two extreme positions 40.1 and 40.2 of the rotary slide can be varied by the manufacturer in order to adapt the device by positioning of the corresponding stops.

Figure 4A:
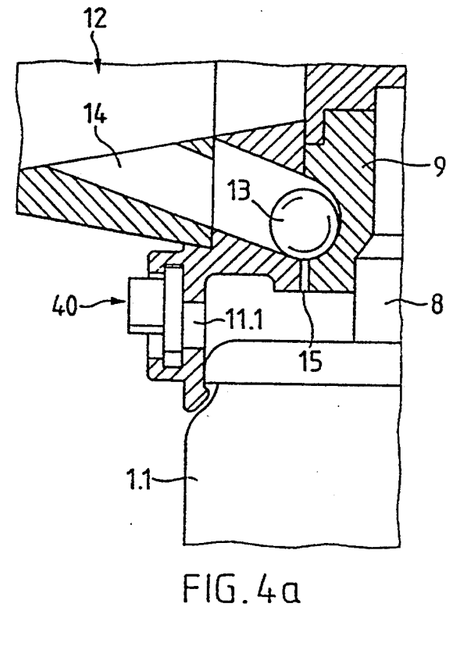
Figure 4B:
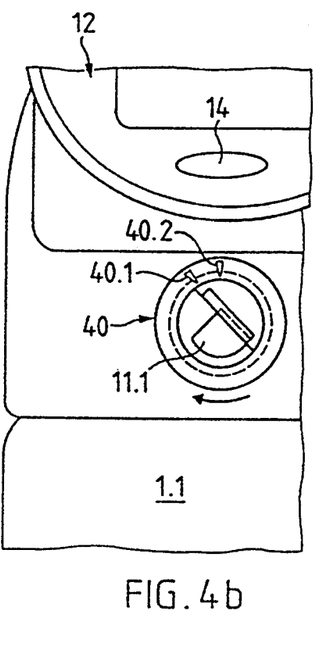
Figure 4C:
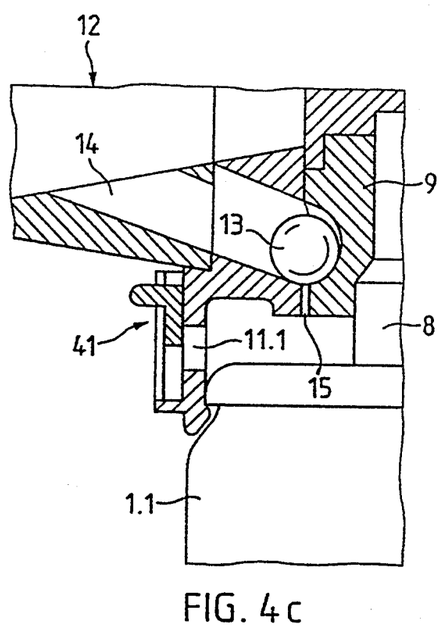
Figure 4D:
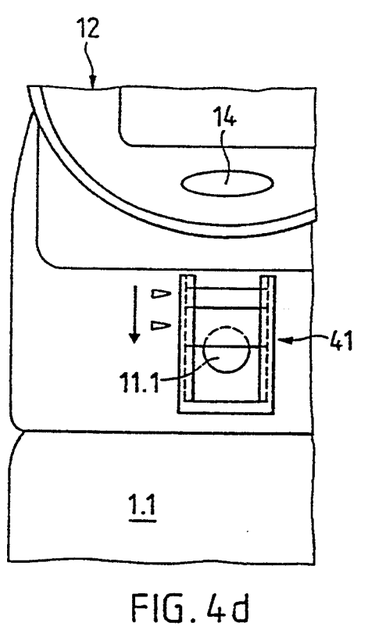

FIGS. 4c and d show details corresponding to FIGS. 4a and b, but for choking the air flow, in this embodiment given by way of example, a simple slide 41 is provided which closes the air hole 11.1 (here with a round cross-section) more or less according to the setting and thus acts as a choke. Movement of the slide 41 in the direction of the arrow effects an increase in the inhalation strength necessary to release the positive locking device.

The method according to the invention can provide a treatment for the nebulized preparation in which droplets or particles which are too large to be inhaled are separated, and by turbulence an aerosol is obtained which is as stable as possible. To carry out this treatment, the interior of the mouthpiece must be suitably formed. in this interior, the nebulized preparation is guided by the nozzle 9.1 into the mouth of the inhaling person. It has proven advantageous so to form this interior that the nebulized preparation is diverted and is guided past baffles. The optimum treatment of the nebulized preparation is very dependent on the type of preparation, on the pressure and speed conditions arising from nebulization, and on the size of the dose. Suitable means (suitably formed mouthpiece, baffles, deflecting faces, absorption faces etc.) must be empirically tested and used accordingly.

Figure 5A:
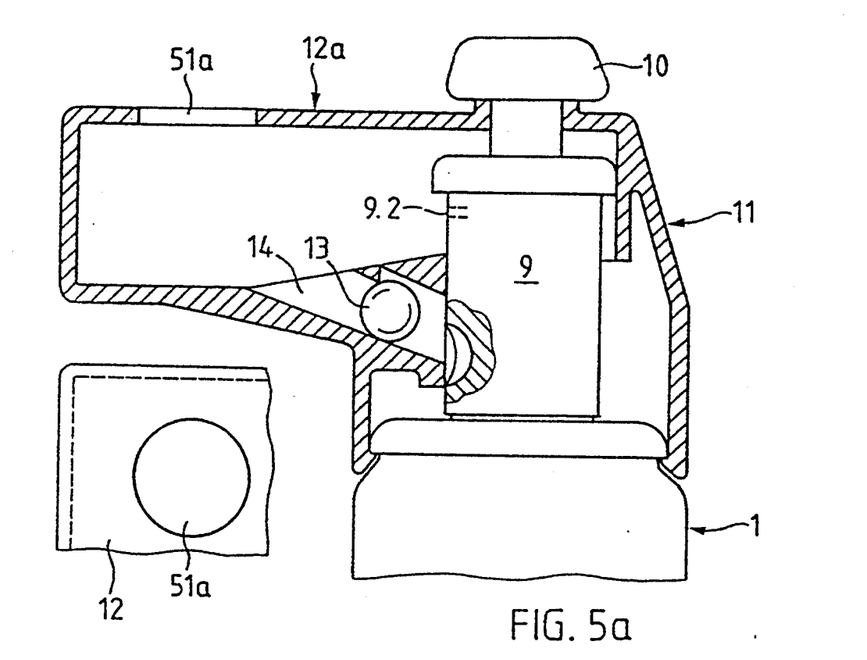
Figure 5B:
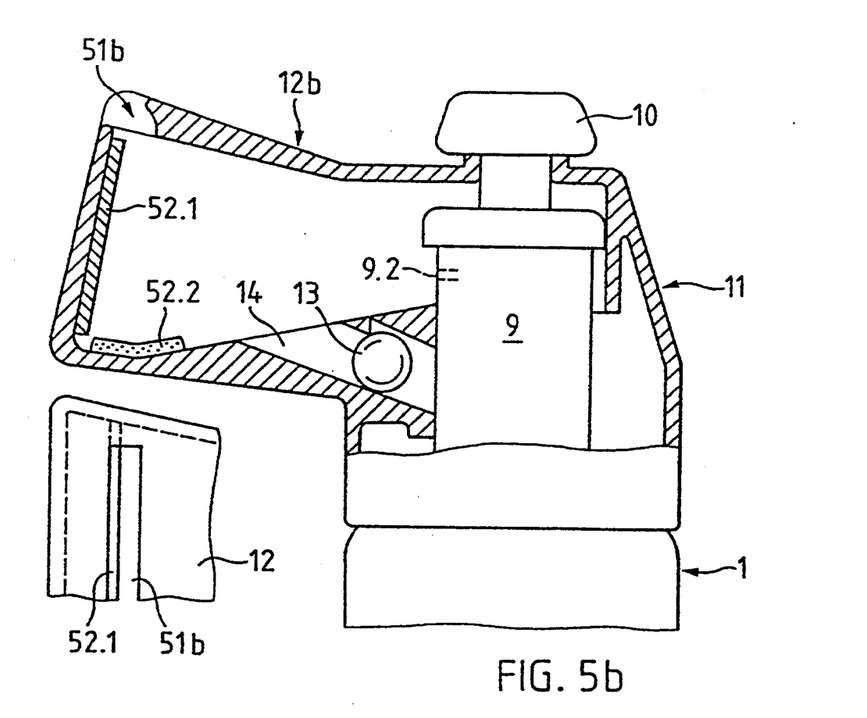
Figure 5C:
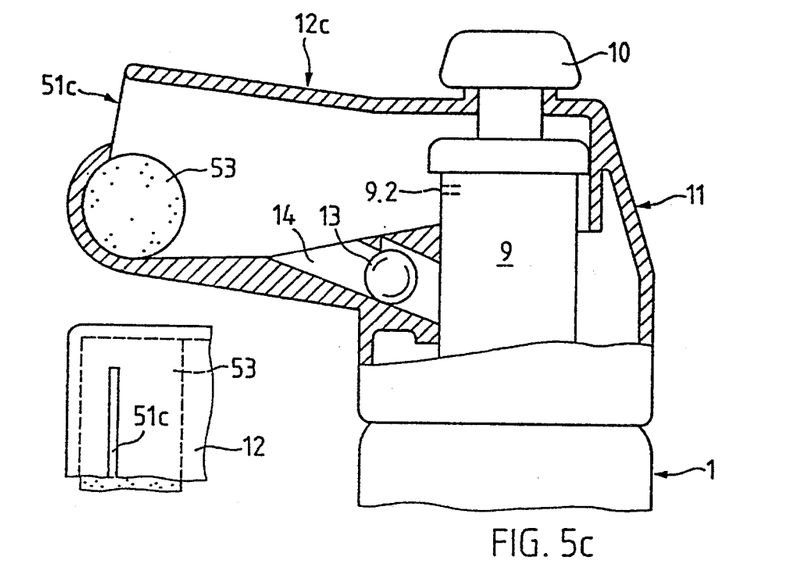

FIGS. 5a to c show various embodiments of mouthpieces, given by way of example, in which deflection and swirling are imposed by suitable mechanical means. In each case, the upper part of the inhalation device is shown in section and the part of the mouthpiece with the opening is shown in plan.

The embodiment shown in FIG. 5a has a mouthpiece 12a, whose round aperture 51a is at the top in the inhalation position. The nebulized preparation hits the wall opposite the nozzle 9.2 and is deflected through approx. 90°. The deflecting face may in this case be blank or coated with an absorption agent. On a blank deflecting face, the droplets or particles of the nebulized preparation are deflected without losing much speed, whereas an absorption agent brakes the droplets or particles and absorbs those that are too large. Suitable absorption means may consist, for example, of sinter material, cellulose or gauze.

The embodiment shown in FIG. 5b has a mouthpiece 12b, whose slot-like aperture 51b is also located at the top. The advantage of a slot-like aperture so located is that the nebulized preparation is caught close to the deflecting face. The deflecting face is coated with an absorber 52.1 and further comprises a soaking-up agent 52.2, which absorbs droplets or preparation remaining in the interior of the mouthpiece.

The embodiment shown in FIG. 5c has a mouthpiece 12c, whose aperture 51c formed as a wide slot is mounted in the wall opposite the nozzle 9.2. But in this case, the aperture 51c and the nozzle 9.2 are at different heights, so that at least some of the nebulized preparation bounces off an absorber roll 53 mounted below the aperture 51c and is deflected. In a mouthpiece interior so formed, the preparation is also swirled.

Figure 6A:
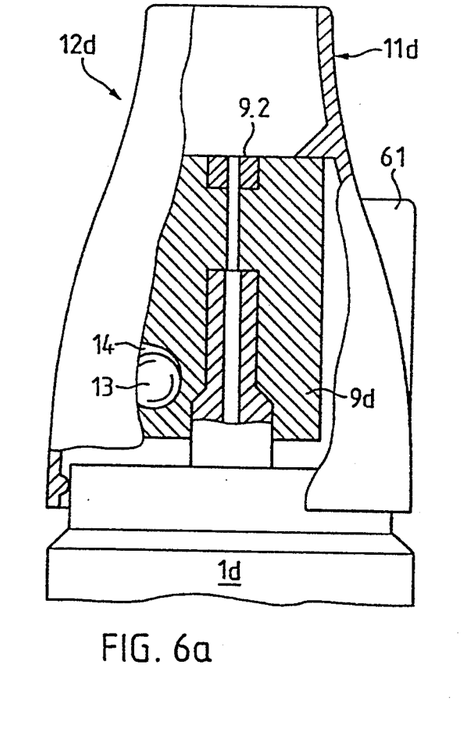
Figure 6B:
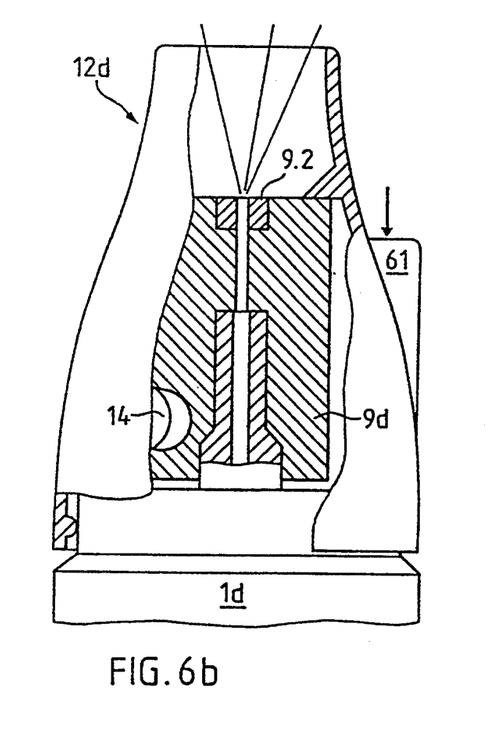

All the embodiments of the device according to the invention described by way of example so far have a nozzle which is horizontally oriented in the inhalation position and a suitably angled nozzle bore system. Obviously, other embodiments are conceivable, in which the nozzle has a different, for example vertical, direction. FIG. 6 shows such an embodiment. The nozzle 9.2 and the mouthpiece 12d are oriented vertically at the top (inhalation device in the inhalation position). Actuation is via a pressure button 61 mounted laterally on the housing 11d. FIG. 6a shows the inhalation device (partly in section) in the locked position, i.e. with the ball 13 in the positively locking position, FIG. 6b in the active position, i.e. with the button 61 depressed and the ball 13 moved out of the positively locking position. It should be noted that in this embodiment, by actuation of the pressure button 61, the housing 11d and the mouthpiece 12d with the nozzle head 9d are moved relative to the reservoir 1d.

Figure 7A:
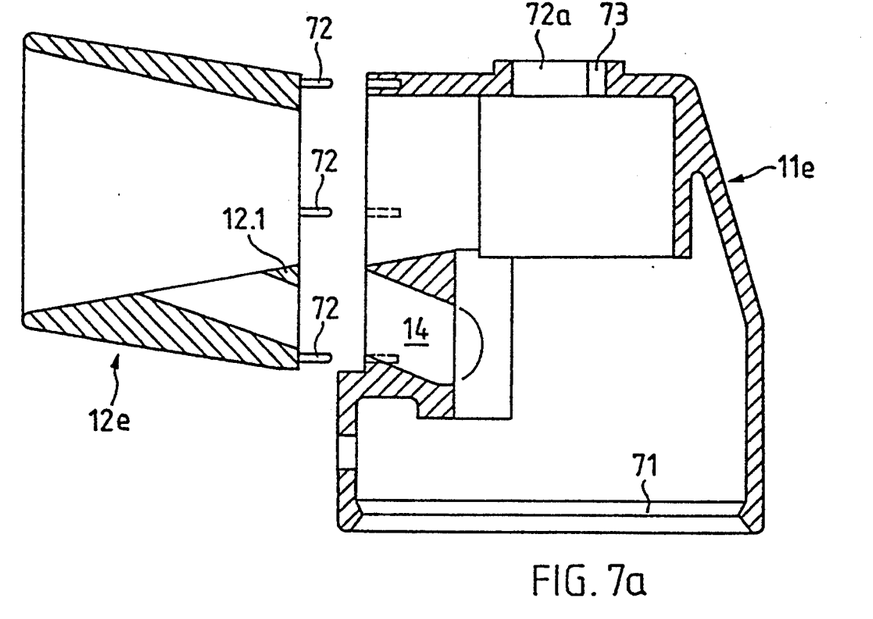

To manufacture the modified embodiment of the inhalation device according to the invention shown in FIGS. 2 and 3, two processes are proposed by way of example. FIGS. 7a and b show the parts to be specially manufactured for the two manufacturing processes and comprising in both cases the housing 11, the mouthpiece 12 and the ball 13 (not shown). In addition, a known device for dosing and nebulizing an inhalation preparation is required. If the moulding in the nozzle head 9 that forms part of the ball chamber 14 cannot be mounted on the standard commercial nozzle head, the outer piston 8 must be extended in order that a locking part 9" of the nozzle head can be mounted between the nozzle head part 9' belonging to the standard commercial device and the reservoir 1.

FIG. 7a shows a housing 11e consisting of one part and a like mouthpiece 12e. It should be noted that the stop 12.1 is integral with the mouthpiece. To assemble, the housing 11e is pushed over the dosing device without a pressure button. A comb 71 on the housing 11e engages in a corresponding groove in the supply vessel. In order to permit assembly with precise positioning of the two parts of the ball chamber, the aperture of the housing is provided with a position cam 73, which fits into a corresponding groove in the neck of the pressure button. After assembly of the housing, the pressure button is mounted on its neck. Then the ball is inserted into the parts of the ball chamber 14 let into the housing 11e and the nozzle head, and last of all the mouthpiece 12e is mounted, which to this end is provided with pins 73, for example, which fit into corresponding holes in the housing 11e. The two parts can also be welded. The advantage of a reversible connection between the housing and mouthpiece is that the device can be reconfigured even after manufacture by the insertion of a different ball.

Figure 7B:
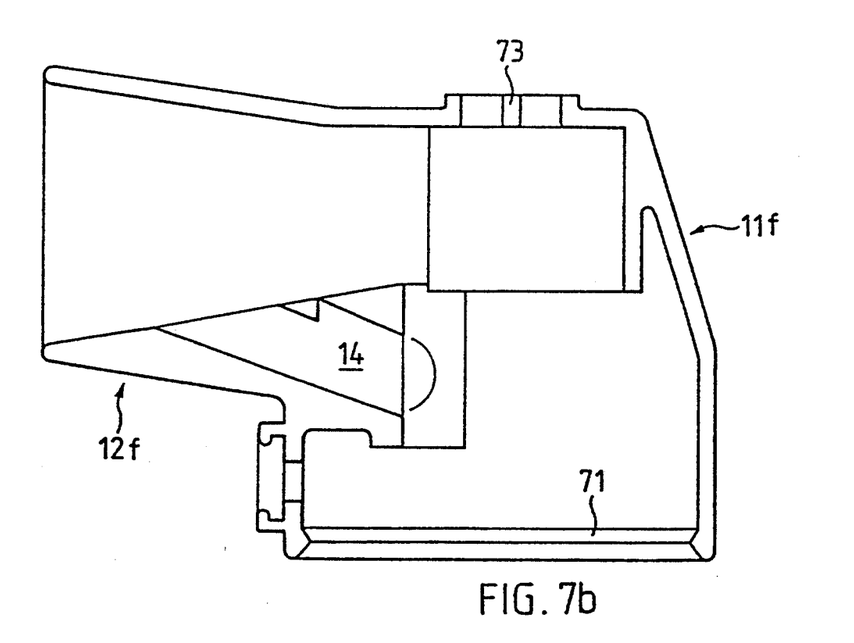

FIG. 7b shows one of two mirror-symmetrical parts, which have to be manufactured for the second manufacturing process given by way of example. This part comprises one half of the housing 11f and one half of the mouthpiece 12f, the planes of symmetry representing the separating line between the two corresponding halves. To assemble the inhalation device, a known dosing and nebulizing device with a mounted pressure button is so placed in the part illustrated that the comb 71 engages in the corresponding groove in the supply vessel and the positioning cam 73 lies in the corresponding groove in the neck of the pressure button. Then the ball is inserted into the (half-) ball chamber 14 and the second part, which is identical with mirror symmetry to the part illustrated, is pushed over the dosing device and the ball on to the part illustrated, to which end pins are provided on one part and corresponding holes or similar fixing means on the other. The two parts can also be welded. This modified manufacture is particularly advantageous if adjustable choke means and/or more complex locking means than balls are to be fitted.

We claim:

1. A device for dosing and nebulizing a liquid or powdered preparation for inhalation comprising:
   a supply chamber containing a supply of said preparation;

a reservoir means surrounding an outer surface of said supply chamber for supporting said supply chamber;

a housing rigidly connected to said reservoir means;

a mouthpiece provided on said housing;

a means for dispensing and nebulizing a dose of said preparation from said supply chamber into an inhalation airflow generated by a user, said dispensing and nebulizing means sliding relative to said housing along a common interface from a locked position to a dispensing position; and a locking means for maintaining said dispensing and nebulizing means in said locked position, said locking means moving between a blocking position and a disengaged position;

wherein said locking means is in said disengaged position when an inhalation force generated by said inhalation airflow overcomes a locking force of said locking means thereby enabling said dispensing means to move relative to said housing, said locking force being generated by gravity, and wherein said mouthpiece is provided with an absorption means for absorbing excess nebulized preparation from a dose too large for inhalation.

2. A method of dosing and nebulizing a liquid or powdered preparation for inhalation and for increasing the inhalation strength of a user, comprising the steps of:

providing a dose nebulizing device having:

a supply chamber containing a supply of a liquid or powdered preparation;

a reservoir means surrounding an outer surface of said supply chamber for supporting said supply chamber;

a housing rigidly connected to said reservoir means;

a mouthpiece provided on said housing;

a dispensing and nebulizing means for dispensing and nebulizing a dose of said preparation from said supply chamber into an inhalation airflow generated by a user, said dispensing and nebulizing means sliding relative to said housing along a common interface face from a locked position to a dispensing position;

a locking means for maintaining said dispensing and nebulizing means in said locked position, said locking means moving between a blocking position and a disengaged position, said locking means comprising a blocking chamber extending between said dispensing means and said housing, and a blocking means acted on by gravity to exhibit a locking force, said blocking means positioned in said blocking chamber for establishing said blocking position when said blocking means intersects said common interface to prevent relative movement of said dispensing means relative to said housing;

means for adjusting the inhalation force required to move said locking means to said disengaged position, and for increasing the inhalation strength of a user, said adjusting means comprising an air inlet orifice located on an exterior of said device, and a means for varying the size of the air inlet orifice, said locking means being moved from said blocking position to said disengaged position by an inhalation force generated by said inhalation airflow of the user drawing air through said air inlet orifice and overcoming the locking force of said locking means, thereby enabling said dispensing and nebulizing means to move relative to said housing;

inhaling air through said air inlet orifice and exerting an inhalation force on said blocking means of said locking means, said inhalation force being generated by an inhalation airflow of an inhaling user;

releasing said locking means when said inhalation force overcomes a locking force of said blocking means generated by gravity, and thereby moving said locking means between said blocked position and said disengaged position;

activating said dispensing and nebulizing means to discharge and nebulize a dose of said preparation from said supply chamber to said inhalation airflow, wherein said step of activating said dispensing and nebulizing means comprises sliding said dispensing and nebulizing means relative to said housing along said common interface from said locked position to a dispensing position; and variably restricting said air inlet orifice to adjust the inhalation force necessary to disengage said blocking means, said step of variably restricting comprising adjusting the size of said air inlet orifice.

3. The method according to claim 2, further comprising the step of automatically restoring said positive locking device when said locking force exceeds said inhalation force.

4. The method according to claim 2, further comprising the step of restricting said inhalation airflow to adjust said inhalation force.

5. The method according to claim 2, wherein said nebulizing step comprises the step of deflecting said preparation.

6. The method according to claim 2, further comprising the step of absorbing particles of nebulized preparation.

7. The method according to claim 2, further comprising the step of inverting said positive locking device in order to release said positive locking device when said user is unable to overcome said locking force with said inhalation force.

8. A dosing and nebulizing device comprising:

a supply chamber containing a supply of a liquid or powdered preparation;

a reservoir means surrounding an outer surface of said supply chamber for supporting said supply chamber;

a housing rigidly connected to said reservoir means;

a mouthpiece provided on said housing;

a dispensing and nebulizing means for dispensing and nebulizing a dose of said preparation from said supply chamber into an inhalation airflow generated by a user, said dispensing and nebulizing means sliding relative to said housing along a common interface from a locked position to a dispensing position;

a locking means for maintaining said dispensing and nebulizing means in said locked position, said locking means moving between a blocking position and a disengaged position, said locking means comprising a blocking chamber extending between said dispensing means and said housing, and a blocking means acted on by gravity to exhibit a locking force, said blocking means positioned in said blocking chamber for establishing said blocking position when said blocking means intersects said common interface to prevent relative movement of said dispensing means relative to said housing; and means for adjusting the inhalation force required to move said locking means to said disengaged position, and for increasing the inhalation strength of a user, said adjusting means comprising an air inlet orifice located on an exterior of said device, and a means for varying the size of the air inlet orifice, said locking means being moved from said blocking position to said disengaged position by an inhalation force generated by said inhalation airflow of the user drawing air through said air inlet orifice and overcoming the locking force of said locking means, thereby enabling said dispensing and nebulizing means to move relative to said housing.

9. The device according to claim 8, wherein said blocking chamber comprises a first opening at an interior of said mouthpiece, a second opening open to an exterior of said device, said chamber sloping toward gravity from said first opening to said second opening, said blocking means being in interposed between said first and second openings, wherein said inhalation airflow passes from said second opening to said first opening.

10. The device according to claim 9, wherein said first opening is positioned on an axis of a dispensing nozzle provided on said dispensing means.

11. The device according to claim 9, wherein said first opening is positioned offset from an axis of a dispensing nozzle provided on said dispensing means, and a nebulizing means for deflecting said preparation toward said first opening is provided on said axis.

12. The device according to claim 11, wherein an absorption means for absorbing a portion of a dose too large for inhalation is provided on said nebulizing means.

13. The device according to claim 12, wherein said absorption means comprises an absorber roll.

14. The device according to claim 8, wherein said adjustment means comprises a rotary slide mounted in said housing.

15. The device according to claim 8, wherein said adjustment means comprises a lateral slide mounted in said housing.

16. The device according to claim 8, wherein said disengaged position is achieved by inverting said device to provide an emergency activation means for dispensing a dose of said preparation when said user is unable to overcome said locking force with said inhalation force.

* * * * *